United States Patent [19]

Moulai

[11] Patent Number: 5,128,976
[45] Date of Patent: Jul. 7, 1992

[54] OSCILLATION RADIOGRAPHY CAMERA AND METHOD

[75] Inventor: Javad Moulai, Newton, Mass.

[73] Assignee: Brandeis University, Waltham, Mass.

[21] Appl. No.: 657,478

[22] Filed: Feb. 19, 1991

[51] Int. Cl.⁵ .......................................... G01N 23/20
[52] U.S. Cl. ........................................ 378/81; 378/79
[58] Field of Search ................ 378/79, 81, 86, 87, 378/88

[56] References Cited

U.S. PATENT DOCUMENTS 4,475,225 10/1984 Gahy et al. ..................... 378/86

OTHER PUBLICATIONS

Sir Lawrence Bragg, The Crystalline State, vol. III 1968 p. 358.
Arndt et al., J. Appl. Cryst. (1973) 6:457.
Stout and Jensen, In X-ray Structure Determination, Macmillan Publ. Co. Inc. 98, 1968, pp. 122-129.
Charles Supper Co. of Natick, Ma.
Mathieson, Acta Cryst. (1982) A38, 378-387.
Huber X-ray Crystallography Equipment catalogue (1990).
Enraf-Nonius catalogue.

Primary Examiner—Craig E. Church
Attorney, Agent, or Firm—Lyon & Lyon

[57] ABSTRACT

An oscillation radiography camera, and method for oscillation radiography, is provided with a generator adapted to generate a collimated beam of quantum fields, such as X-ray or gamma ray photons, or neutrons. Two or more motors are constructed and arranged to position a sample for exposure to the collimated beam. Each of the motors rotates the sample about an axis, with the motors providing a precise net rotation of the sample to within a degree. A detector is constructed and arranged to detect the quantum fields scattered from the sample.

28 Claims, 2 Drawing Sheets

OSCILLATION RADIOGRAPHY CAMERA AND METHOD

BACKGROUND OF THE INVENTION

The invention relates to oscillation radiography cameras.

A radiograph is "a picture produced on a sensitive surface by a form of radiation other than light." [*Webster's Ninth New Collegiate Dictionary*] For instance, a radiograph is typically "an X-ray or gamma ray photograph," [ibid.] but radiographs can also be made by corpuscular neutron or beta radiation. In either case, whether the radiation is composed of bosons, like photons and nuclei with an even number of nucleons, or composed of fermions, like neutrons, protons, other nuclei with an odd number of nucleons, electrons and positrons, the beam can always be completely characterized by appropriate quantum effects. The sensitive surface on which the radiograph picture is produced can include suitable electronic detector sensor arrays and charge-coupled devices (CCDs) as well as the more usual plates treated with photographic emulsions. Radiography is "the art, act, or process of making radiographs." [ibid.]

When a beam of X-rays or other energetic rays reaches certain material which is transparent to that particular type of beam, it simply goes through that material. Some other material may however, under some conditions, scatter the beam into one or more directions different from the incident beam. This phenomenon of scattering can be utilized to investigate the characteristics of the beam or of the material. In such scattering experiments the goal is to determine how the beam is scattered into the various directions. One method to achieve this goal is to place a photographic film behind the sample of the material such that a picture of the scattered pattern is produced. Since some rays in the beam may pass directly through the film, it is desirable to use a stack of more than one film in order to record all of the rays. In any case, the picture(s) can be inspected either visually or by automatic film scanners via a computer to determine the various aspects of the scattering.

There are several types of cameras known in the radiography art which are designed to measure scattering as discussed above. An oscillation radiography camera is one of several types of radiography cameras distinguished by the manner of moving the sample exposed to the radiation and the detectors of the radiation scattered by the sample. These are discussed generally by Arndt et al., *J. Applied Crystallography* 6:457, 1973. For example, an oscillation camera rotates the sample, to a small extent (which depends on the specific sample being radiographed, but generally is in the range of from around 0.5° up to around 2°), back and forth in an oscillatory fashion, about a fixed axis, during exposure of the sample to the radiation. A rotation camera rotates the sample, to a larger extent (which also depends on the specific sample being radiographed, but generally is in a range greater than or equal to around ten times the range for oscillation cameras, i.e. from around 5° to around 20° or more), back or forth, about a fixed axis, during exposure of the sample to the radiation.

Stout and Jensen, In *X-ray Structure Determination*, Macmillan Publ. Co. Inc. 98, 1968 generally describe a precession camera which precesses the sample around in the beam of radiation. Stout and Jensen also describe a Weissenberg camera (at page 83) which also causes movement of the sample exposed to the radiation. Both the precession and Weissenberg cameras cause movement of the sample being exposed and, during such exposure, movement of the detectors recording the scattered beam.

Oscillation cameras, such as those made by Charles Supper Co. of Natick, Mass., and Enraf-Nonius in Europe, conventionally use a single motor to oscillate the sample about an axis perpendicular to the beam. A combination camera made by Charles Supper Co. of Natick, Mass., combines two motors, one to effect oscillation, and the other to effect precession. The motors are not used simultaneously; the oscillation exposures are taken while the precession motion is disabled, and the precession exposures are taken while the oscillation motion is disabled.

SUMMARY OF THE INVENTION

The present invention provides an apparatus which gives enhanced accuracy in oscillation radiography, due in part to the increased amount of data that can be obtained using the apparatus and in part due to enhanced accuracy. The apparatus generally has two or more independently programmed motors which allow oscillations of a sample connected to those motors about substantially any axis of orientation of the sample. In one example, the motors have coincident axes of oscillation which allow coarse motions of each motor effecting movement of the sample to be combined into a resultant much finer motion of the sample. In another example, the motors are coordinated to provide correlated simultaneous fine motions of the sample and the detector which sufficiently enhances the accuracy of the signals detected to allow use of photographic films rather than electronic devices.

The apparatus of the present invention enables experimenters to obtain not only angular information about the scattered beam, but also its intensity. Thus, it differs from precession and Weissenberg cameras, since the quality of the signals recorded is sufficient to obtain intensity data. This is due in part to correlation of motions between the sample and the detector that enhances quality of the intensity measurements.

In general, in one aspect, the invention features an oscillation radiography camera having a generator adapted to generate a collimated beam of quantum fields, and a first, and second motor constructed and arranged to position a sample for exposure to the collimated beam of quantum fields. Each of the motors rotates the sample about an axis, with the motors providing a precise net rotation of the sample to within a degree. A detector is constructed and arranged to detect the quantum fields scattered from the sample.

In another aspect, the invention features an oscillation radiography camera having a generator adapted to generate a collimated beam of quantum fields, a detector constructed and arranged to detect the quantum fields scattered from a sample, a first motor constructed and arranged to position the sample in the collimated beam, and a second motor constructed and arranged to position the detector. The two motors are controlled by one computer in a correlated fashion, such that motion of one motor correlates with simultaneous motion of the other motor. Such correlation reduces quantum noise and statistical noise in signals detected by the detector compared to such noise in uncorrelated motors, or where only one motor is provided. For example, oscillation of the detector in phase with oscillation of the sample (i.e. in the same direction and with the same angular amplitude) will cause all the reflected rays of each reflection angle to affect the same picture element (pixel) of the detector, enhancing the signal-to-noise ratio by making the spot on the detector sharper while preventing overlap in case there are too many reflections. On the other hand, oscillation of detector with a larger angular amplitude than oscillation of the sample will record the reflected rays on a larger area of the detector (several pixels for each reflection angle), decreasing the intensity at each pixel while preserving the overall integrated intensity of any reflection, in case the reflections are so intense as to otherwise saturate, and possibly damage, the detector.

These correlations serve to reduce quantum and statistical noise in detected signals in the detector. In general, because of the discrete nature of the quanta involved, X-ray photons for example, there is an inherent quantum noise associated with the non-continuous arrival of scattered X-ray photons, as well as an inherent statistical noise associated with fluctuations as large as $N^{\frac{1}{2}}$ in the number of X-ray photons detected when the total number of X-ray photons detected is N.

In yet another aspect, the invention features an oscillation radiography camera having a generator adapted to generate a collimated beam of quantum fields, and a first and second motor constructed and arranged to position a sample for exposure to the collimated beam of quantum fields. Each of the motors rotates the sample about an axis, the motors providing a precise net rotation to within a degree. A detector is constructed and arranged to detect the quantum fields scattered from the sample. A third motor is also provided, constructed and arranged to position the detector. A computer controls and correlates these movements. The correlation serves to reduce quantum noise and statistical noise in detected signals in the detector as discussed above.

In preferred embodiments, the oscillation radiography camera as described above is designed so that the first motor is adapted to rotate about a first axis, and the second motor to rotate about a second axis, where the second axis is disposed at a different orientation from the first axis; alternatively, the first and second motors rotate about the same axis; and the detector is a photographic medium, an electronic medium, or a charge-coupled device.

In other embodiments, the correlated simultaneous motion of the motor constructed and arranged to position the detector has substantially the same or greater angular amplitude as the oscillatory motion of the samples.

In related aspects, the invention features methods for oscillation radiography which include generating a collimated beam of quantum fields, positioning a sample for exposure to the quantum fields, oscillating that sample in the quantum fields using two motors which are adapted to oscillate the sample about an axis while maintaining the sample in a fixed location, and detecting the quantum fields scattered from a sample with a detector. Alternatively, the sample may be positioned in the quantum fields and the motion of a first motor constructed and arranged to position the sample is correlated with simultaneous motion of a second motor constructed and arranged to position the detector. These two methods may be combined in a related aspect such that two motors cause oscillation of the sample about one or more axes and the motions of such motors are correlated with motions of the detector.

Other features and advantages of the invention will be apparent from the following description of the preferred embodiments thereof, and from the claims.

DESCRIPTION OF THE PREFERRED EMBODIMENT

The drawings will first briefly be described.

DRAWINGS

Figure 1:
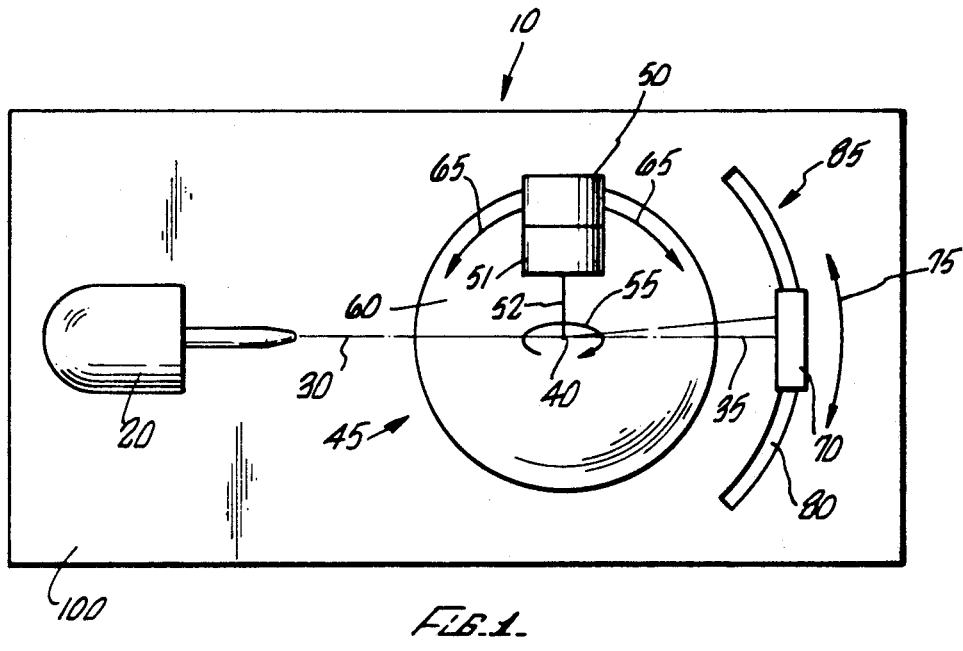
Figure 2:
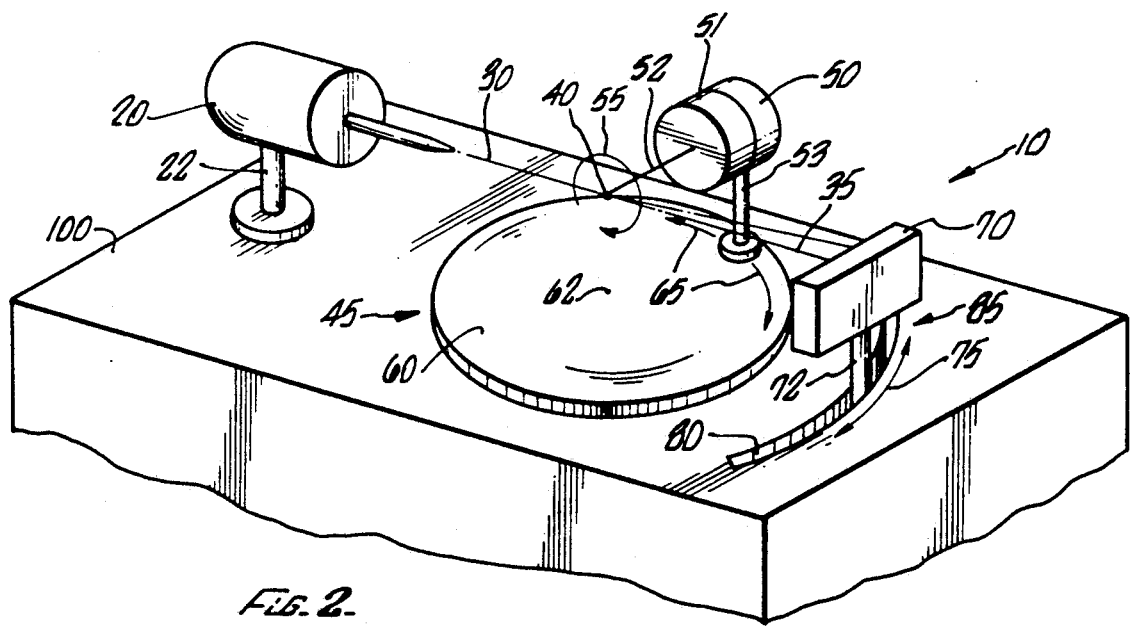
Figure 3:
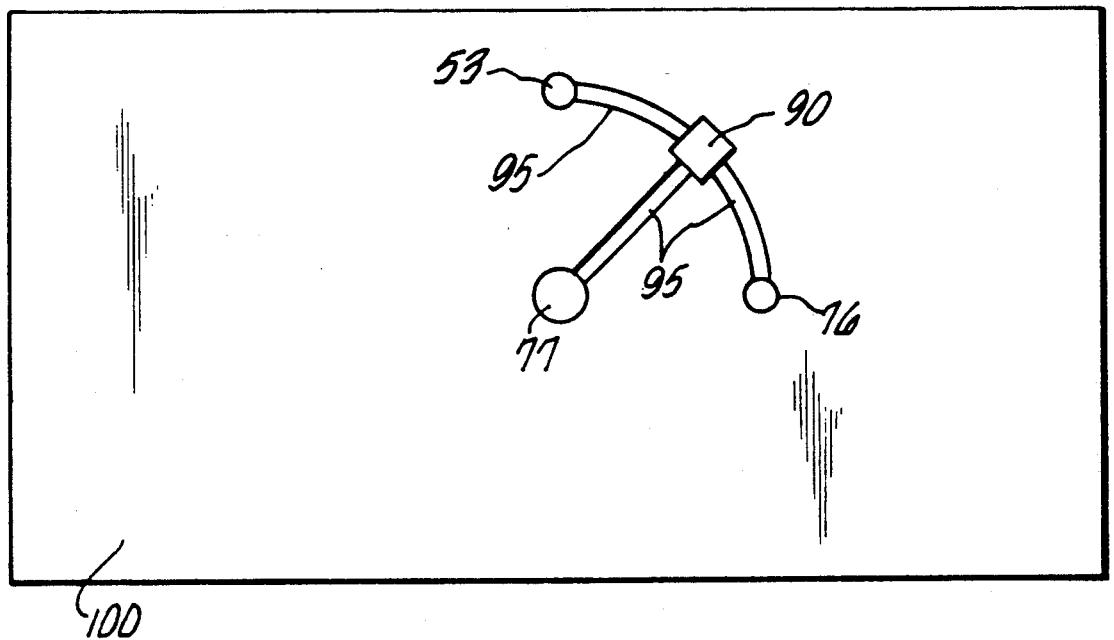

FIGS. 1 and 2 show a top and isometric view of a preferred embodiment of the invention; and FIG. 3 shows a view of the computer cables and controls for the embodiment of FIG. 1.

STRUCTURE

Referring to FIGS. 1 and 2, a camera 10 is formed with a base platform 100. At one end of platform 100 is an X-ray source 20 which is fixedly mounted to platform 100 and provides a collimated beam of X-rays 30. In the center of platform 100 is a rotatably mounted turntable sample holder 45, and adjacent to this a slidably movable detector constellation 85. The collimated beam of X-rays 30 has an average energy in the range of from around 2.00 keV to around 20.00 keV. The collimated beam is incident on a sample 40, for example, a solid crystalline sample of a macromolecule of interest, mounted at the end of a spindle 52. Spindle 52 is rotatable, by a first spindle motor 50 and a second spindle motor 51, about the longitudinal axis of spindle 52, as indicated by arrow 55. The beam scattered by the sample 40 is represented generally by a region 35, and is detected by a detector 70. Detector 70 is movable, as indicated by the arrows 75, along a grooved track 80.

As shown particularly in FIG. 2, source 20 is fixedly mounted on a source support 22 affixed to base platform 100. First spindle motor 50 and second spindle motor 51 are fixedly mounted on spindle motor support 53 affixed to turntable 60. Turntable 60 is movably mounted on base platform 100, rotatable about turntable center 62, as indicated by arrows 65. A turntable motor 77, as shown in FIG. 3, for causing a rotating motion of the turntable 60 is disposed within base platform 100.

Sample 40 at the end of spindle 52 is generally located vertically above turntable center 62. The axes of the rotations of spindle 52 and turntable 60 are substantially mutually orthogonal.

Detector 70 is fixedly mounted on a detector support 72 movably disposed in a grooved track 80. Detector support 72 is moved along grooved track 80 by a detector motor 76, as shown in FIG. 3, disposed within base platform 100. For example, detector support 72 can be mounted on another turntable (not shown), or sector of a turntable, disposed within base platform 100, which turntable, or sector of a turntable, is rotatable by the detector motor 76. Detector motor 76 is linked by a computer link 95 to computer 90, which is also linked by other computer links 95 to turntable motor 77 and spindle motor support 53, which in turn connects spindle motors 50 and 51 with computer 90, as illustrated in FIG. 3, showing the underside of platform 100. Computer 90 (e.g., any standard computer, such as an IBM PC) effects the correlated motions of spindle motors 50 and 51, turntable motor 77, and detector motor 76, communicating with the respective motors through computer links 95. The control modules required for such correlation can be obtained from any motor manufacturer or the like; the necessary software can also be obtained from such manufacturer or created by one of ordinary skill in the art without undue experimentation.

The first spindle motor 50 and second spindle motor 51 each rotate the spindle about the same axis. Both motors 50 and 51 are stepper motors. Coarser movements of individual stepper motors, such as those manufactured by Superior Electric, Bristol, Conn., and New England Affiliated technologies, Div. of Instrument Industries, Inc., Lawrence, Mass., are combined to yield a finer, more precise overall movement of this group of motors. For example, with these two stepper motors, say spindle motor 50 has a step size of 0.005°, and spindle motor 51 has a step size of 0.004°. Then, a clockwise step of spindle motor 50 of 0.005° followed by a counterclockwise step of spindle motor 51 of 0.004° results in a net clockwise step of 0.001°. Using these same two motors, a rotation of the spindle through 0.2°, which must be speedily executed, can be readily effected by stepping each motor substantially simultaneously in the same direction 20 and 25 times, respectively, a swifter procedure than individually stepping spindle motor 50 forty times or spindle motor 51 fifty times.

A person of ordinary skill in the art of oscillation radiography will appreciate that the turntable motor 77 and the detector motor 76 can likewise be replaced by groups of two or more motors, with similar advantages gained.

The correlation of the movements of sample 40 with fine motions of detector 70, enhances and increases the accuracy of the resulting radiograph. In general, because of the discrete nature of the quanta involved, X-ray photons for example, there is an inherent quantum noise associated with the non-continuous arrival of scattered X-ray photons, as well as an inherent statistical noise associated with fluctuations as large as $N^{\frac{1}{2}}$ in the number of X-ray photons detected when the total number of X-ray photons detected is N. Both of these sources of noise are minimized by averaging exposures of the sample 40 over periodic variations in orientation during fine oscillations of the sample 40 and by correlating the fine motions of the sample 40 with precise, fine motions of the detector 70. For example, oscillation of detector 70 in phase with oscillation of the sample 40 (i.e. in the same direction and with the same angular amplitude) will cause all the reflected rays of each reflection angle to affect the same pixel of the detector 70, enhancing the signal-to-noise ratio by making the spot on the detector sharper while preventing overlap in case there are too many reflections. On the other hand, oscillation of detector 70 with a larger angular amplitude than oscillation of the sample 40 will record the reflected rays on a larger area of the detector 70 (several pixels for each reflection angle), decreasing the intensity at each pixel while preserving the overall integrated intensity of any reflection, in case the reflections are so intense as to otherwise saturate, and possibly damage, the detector 70.

The correlations of the fine motions of the sample 40 and the precise, fine motions of the detector 70 are such that even photographic detectors can be used to advantage in the invention.

OPERATION

In operation, source 20 generates a collimated beam of X-rays 30 which are scattered by sample 40 at the end of spindle 52 and subsequently detected by detector 70. During exposure of sample 40 to X-rays 30, spindle motors 50 and 51 together with turntable motor 77 oscillate sample 40 about any instantaneous axis which can be formed from the vector sum of the instantaneous rotations indicated generally by arrows 55 and 65. Detector motor 76 and computer 90 causes detector 70 to be appropriately moved as indicated by arrows 75 along grooved track 80 while sample 40 is exposed to X-rays 30 and oscillated by spindle motors 50 and 51 and turntable motor 77, which motors are also controllable by the same computer. When sample 40 has been sufficiently exposed to X-rays 30, sample 40 is rotated and exposed another time, or is changed for a different sample, and another film is made ready in detector 70.

A list of the computer programs suitable for the data processing of the image information obtained with the apparatus described above is as follows:

The CCP package (with a flexible geometry built in allowing for a change of oscillation axis) from
Catalogue of Crystallographic Programs
Laboratory of Molecular Biology
Medical Research Council
Cambridge University, England The MADNESS package either from
J. W. Pflugrath
Cold Spring Harbor Laboratory
P.O. Box 100
Cold Spring Harbor, N.Y. 11724
or
A. Messerschmidt
Max Planck Institute fur Biochemie
D 8033 Martinsried, Germany The XENSYS and BUDHA packages from
Structural Molecular Biology Laboratory
Biochemistry Department
Harvard University
Cambridge, Mass. 02138

Other embodiments are within the following claims.

I claim:

1. An oscillation radiography camera comprising
a generator adapted to generate a collimated beam of quantum fields,
a first motor and a second motor constructed and arranged to position a sample for exposure to said collimated beam of quantum fields, wherein each said motor is adapted to oscillate said sample about an axis, and
a detector constructed and arranged to detect said quantum fields scattered from said sample.

2. An oscillation radiography camera comprising
a generator adapted to generate a collimated beam of quantum fields,
a detector constructed and arranged to detect said quantum fields scattered from a sample,
a first motor constructed and arranged to oscillate and position said sample in said collimated beam,
a second motor constructed and arranged to position said detector, and
a computer adapted to correlate motion of said first motor with simultaneous motion of said second motor, said correlated motion of said motors reducing quantum noise and statistical noise in detected signals in said detector compared to an uncorrelated motion of said motors.

3. An oscillation radiography camera comprising
a generator adapted to generate a collimated beam of quantum fields,
a first motor and a second motor constructed and arranged to position a sample for exposure to said collimated beam of quantum fields, wherein each said motor is adapted to oscillate said sample about an axis, a detector constructed and arranged to detect said quantum fields scattered from said sample, a third motor constructed and arranged to position said detector, and a computer adapted to correlate motion of said first motor and said second motor with simultaneous motion of said third motor, said correlated motions of said motors reducing quantum noise and statistical noise in detected signals in said detector compared to an uncorrelated motion of said motors.

4. The camera of claim 1 or 3 wherein said first motor is adapted to oscillate said sample about a first axis, and said second motor is adapted to oscillate said sample about a second axis, said second axis at a different orientation from said first axis.

5. The camera of claim 1 or 3 wherein said first motor is adapted to oscillate said sample about an axis and said second motor is adapted to oscillate said sample about said axis.

6. The camera of claim 1, 2 or 3 wherein said detector is a photographic medium.

7. The camera of claim 1, 2 or 3 wherein said detector is an electronic medium.

8. The camera of claim 7 wherein said electronic medium is a charge-coupled device.

9. The camera of claim 2 wherein said computer is adapted to provide simultaneous motion of said second motor with substantially the same angular amplitude as the oscillatory motion of said sample.

10. The camera of claim 3 wherein said computer is adapted to provide simultaneous motion of said third motor with substantially the same angular amplitude as the oscillatory motion of said sample.

11. The camera of claim 2 wherein said computer is adapted to provide simultaneous motion of said second motor with a substantially greater angular amplitude than the oscillatory motion of said sample.

12. The camera of claim 3 wherein said computer is adapted to provide simultaneous motion of said third motor with a substantially greater angular amplitude than the oscillatory motion of said sample.

13. The camera of claim 1 or 3, wherein said motors are constructed and arranged to provide a precise net rotation of said sample to within a degree.

14. The camera of claim 1 or 3, wherein said first and second motors are constructed and arranged to simultaneously position said sample.

15. A method for oscillation radiography comprising the steps of generating a collimated beam of quantum fields, positioning a sample for exposure to said collimated beam of quantum fields, oscillating said sample in said collimated beam using a first motor and a second motor, wherein each said motor is adapted to oscillate said sample about an axis while maintaining said sample in a fixed location, and detecting said quantum fields scattered from said sample with a detector.

16. A method for oscillation radiography comprising the steps of generating a collimated beam of quantum fields, positioning and oscillating a sample in said beam, detecting said quantum fields scattered from a sample with a detector, and correlating motion of a first motor constructed and arranged to position said sample exposed to said collimated beam of quantum fields with simultaneous motion of a second motor constructed and arranged to position said detector, said correlated motions of said motors reducing quantum noise and statistical noise in detected signals in said detector compared to an uncorrelated motion of said motors.

17. A method for oscillation radiography comprising the steps of generating a collimated beam of quantum fields, positioning a sample for exposure to said collimated beam of quantum fields, oscillating said sample in said collimated beam using a first motor and a second motor, wherein each said motor is adapted to oscillate said sample about an axis while maintaining said sample in a fixed location, detecting said quantum fields scattered from said sample with said detector, and correlating motion of said first motor and said second motor constructed and arranged to position said sample with simultaneous motion of a third motor constructed and arranged to position said detector, said correlation reducing quantum noise and statistical noise in detected signals.

18. The method of claim 15 or 17, further comprising the steps of oscillating said first motor about a first axis, and said second motor about a second axis, said second axis at a different orientation from said first axis.

19. The method of claim 15 or 17, said first motor oscillating about an axis and said second motor also oscillating about said axis.

20. The method of claim 15, 16 or 17 wherein said detector further comprises a photographic medium.

21. The method of claim 15, 16 or 17 wherein said detector further comprises an electronic medium.

22. The method of claim 21 wherein said electronic medium is a charge-coupled device.

23. The method of claim 16 wherein said correlated simultaneous motion of said second motor has substantially the same angular amplitude as the oscillatory motion of said sample.

24. The method of claim 17 wherein said correlated simultaneous motion of said third motor has substantially the same angular amplitude as the oscillatory motion of said sample.

25. The method of claim 16 wherein said correlated simultaneous motion of said second motor has a substantially greater angular amplitude than the oscillatory motion of said sample.

26. The method of claim 17 wherein said correlated simultaneous motion of said third motor has a substantially greater angular amplitude than the oscillatory motion of said sample.

27. The method of claim 15 or 17, said motors providing a precise net rotation of said sample to within a degree.

28. The method of claim 15 or 17, said first and second motors simultaneously positioning said sample.

* * * * *